(12) United States Patent
Goddijn et al.

(10) Patent No.: US 6,559,364 B1
(45) Date of Patent: May 6, 2003

(54) PRE- AND POSTHARVEST INHIBITION OF REMOBILISATION OF STORAGE COMPOUNDS

(75) Inventors: Oscar Johannes Maria Goddijn, Leiden (NL); Hendrik Tigelaar, Utrecht (NL); Klaus-Peter Krause, Hanhofen (NL); Cornelis Maria Petrus Van Dun, Roosendaal (NL)

(73) Assignee: Mogen International N.V., Ridderkirk (NL)

( * ) Notice: Subject to any disclaimer, the term of this patent is extended or adjusted under 35 U.S.C. 154(b) by 0 days.

(21) Appl. No.: 09/529,993

(22) PCT Filed: Oct. 30, 1998

(86) PCT No.: PCT/EP98/07010

§ 371 (c)(1),
(2), (4) Date: Jul. 21, 2000

(87) PCT Pub. No.: WO99/23234

PCT Pub. Date: May 14, 1999

(30) Foreign Application Priority Data

Oct. 30, 1997 (EP) .............................................. 97203371

(51) Int. Cl.$^7$ ......................... C12N 15/82; C12N 15/84; C12N 15/31; A01H 5/00; C12P 19/04
(52) U.S. Cl. .................... 800/317.2; 800/278; 800/284; 800/287; 800/288; 800/290; 800/294; 800/300; 435/101; 435/468; 435/469
(58) Field of Search ................................ 800/278, 284, 800/287, 288, 290, 317.2, 294, 300; 435/101, 468, 469

(56) References Cited

FOREIGN PATENT DOCUMENTS

| | | |
|---|---|---|
| DE | 42 13 444 | 10/1993 |
| EP | 0 577 915 | 1/1994 |
| EP | 0 784 095 | 7/1997 |
| WO | WO 93 06711 | 4/1993 |
| WO | WO 93 17093 | 9/1993 |
| WO | WO 94 28146 | 12/1994 |
| WO | WO95/06126 | * 3/1995 |
| WO | WO 95 24487 | 9/1995 |
| WO | WO 96/00789 | 1/1996 |
| WO | WO 96/12812 | 5/1996 |
| WO | WO 96/17069 | 6/1996 |
| WO | WO 97/24448 | 7/1997 |
| WO | WO 97/42326 | 11/1997 |

OTHER PUBLICATIONS

Sprenger Et Al. FEBS Letters 400(3): 355–358, 1997.*
Monger Et Al. pp. 12–14 In: Agri–Food Quality, Spec. Pub. No. 179, Royal Soc. Chem. : Cambridge, UK, 1996.*
Vijn Et Al. Plant Journal 11(3): 387–398, 1997.*
Jacq Et Al. Plant Cell Reports 12(11):621–624, 1993.*
Krens Et Al. Plant Science 116(1):97–106, 1996.*
Mian, A. J. Sci. Int. (Lahore) 5(3):281–284, 1993.*
Hall Et Al. Nature Biotechnology 14(9):1133–1138, Sep. 1996.*
Romero, C. et al., Planta, vol. 201, No. 3, 1997, pps. 293–297.
Goddijn, O.J.M. et al., Plant Physiology, vol. 113, No. 1, Jan. 1997, pps. 181–190.
Heifetz, P.B. et al., Supplement to Plant Physiology, vol. 114, No. 3, Jul. 1997, pp. 308.

* cited by examiner

*Primary Examiner*—David T. Fox
(74) *Attorney, Agent, or Firm*—Hale and Dorr LLP

(57) ABSTRACT

This invention describes a method to prevent post-harvest sprouting in potato by transforming the potato plant with a gene coding for trehalose phosphate synthase.

7 Claims, 1 Drawing Sheet

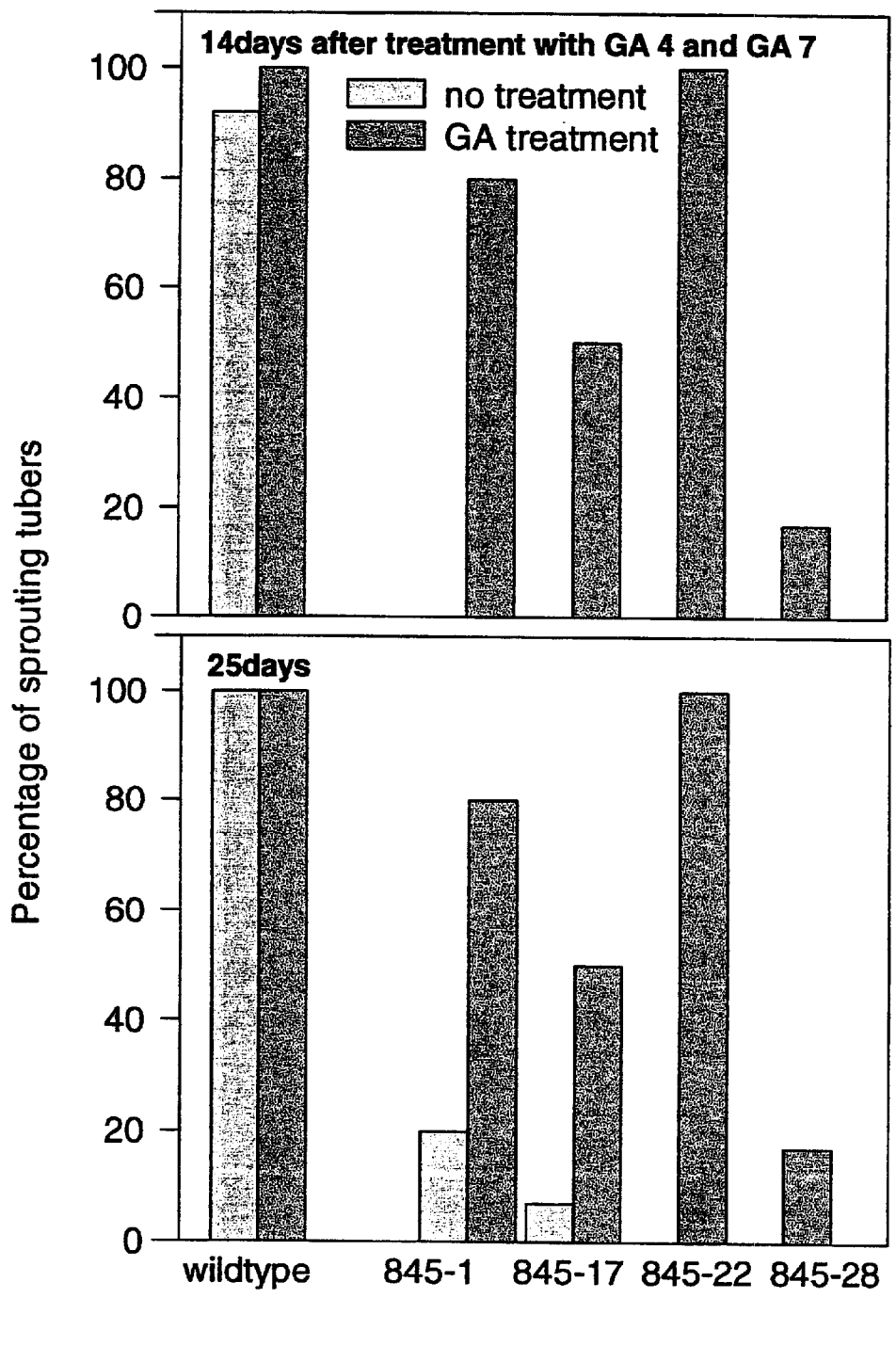

PRE- AND POSTHARVEST INHIBITION OF REMOBILISATION OF STORAGE COMPOUNDS

FIELD OF THE INVENTION

This application is concerned with the pre- and postharvest inhibition of remobilisation of storage compounds. Especially, the application describes the prevention of sprouting, especially in vegetatively propagated plants by transforming them with recombinant DNA and a method to restore sprouting in these lines.

BACKGROUND ART

In traditional breeding as well as in agricultural genetic engineering the major goal is to obtain crops with a high yield, which generally means that the goal has been to increase storage of the plant in the organs of the plant that are used for storage, such as the tubers in potato, the taproot in sugarbeet, and the leaves in leafy crops such as lettuce. However, other processes in plants, such as flowering and or sprouting, often give a yield penalty.

Sprouting normally can be inhibited by cold storage at very low temperatures (slightly above freezing). Cold storage is not only expensive, but also inflicts deleterious effects upon storage organs, which render them unsuitable for further processing or result in yield losses of commercial products as starch. For example when potato tubers are subjected to cold temperatures, they convert starch to reducing sugars, a phenomenon known as 'cold sweetening'. The development of reducing sugars is very undesirable because during baking and frying e.g. the Maillard reaction occurs that results in undesired browning.

To prevent cold sweetening potatoes can be stored at higher temperatures, but this results in undesired sprouting. Amongst others, chlorpropham (CIPC) is used by the industry to control tuber sprouting. Although CIPC has been used effectively, it still is considered as an undesirable chemical treatment. All around the world, there is an increasing emphasis on replacing chemical control agents with biological control mechanisms that are safe and more environmentally acceptable.

When considering a genetic approach to inhibit sprouting, it must also be considered that for the development of seed-potatoes sprouting is a desired property, and that thus a mechanism should be at hand which enables seed-potato production but which prevents sprouting in potatoes cultured for consumption or further processing.

SUMMARY OF THE INVENTION

This invention comprises a method to inhibit pre- and postharvest remobilisation of storage compounds. More specifically, the invention comprises a method to prevent sprouting of a plant part by transforming the plant or its ancestor with a recombinant DNA capable of expression of a protein, characterized in that the protein is trehalose phosphate synthase (TPS). More specifically the recombinant DNA comprising the gene coding for TPS is of bacterial, fungal, animal, plant or human origin, preferably derived from *Escherichia coli*. In another embodiment the invention comprises a method to induce sprouting in a plant by providing said plant with recombinant DNA coding for TPS flanked by target sites of a site-specific recombinase and removing the recombinant DNA coding for TPS by providing said plant either through transformation with a gene coding for the corresponding recombinase or through crossing with a plant capable of expressing said recombinase.

Still another embodiment of the invention comprises a method to induce sprouting in a plant by providing a plant with recombinant DNA coding for TPS and subsequently or simultaneously transforming it with a recombinant DNA which comprises a gene coding for a molecule that can neutralize the effect of TPS under control of an inducible promoter and forcing expression of the neutralizing molecule by induction of the inducible promoter. An example of such a neutralizing molecule is trehalose phosphate phosphatase (TPP) or the product of the antisense TPS gene.

Another embodiment of the invention is formed by removing the inhibition of pre- and post-harvest mobilisation of storage compounds by external treatment with compounds that neutralize the inhibitory effect of the expression of the TPS gene. Preferably this is accomplished by applying gibberellic acid. Still another embodiment of the invention is to restore sprouting by wounding.

A further object of the invention is a method to induce sprouting in a plant by providing a plant with recombinant DNA coding for TPS and subsequently or simultaneously transforming it with a recombinant DNA which comprises a gene coding a suppressor under control of an inducible promoter, said suppressor capable of suppressing expression of the TPS and forcing expression of the suppressor by induction of the inducible promoter.

Also the invention provides for plants made by any of the above mentioned methods, specifically vegetatively propagated plants and more specifically potato and onion.

Further the gene coding for TPS can be placed under control of a specific promoter, such as the patatin promoter, which specifically gives expression in the tuber of the potato plant.

Another embodiment of the invention is the inhibition of the catabolism of inulin in chicory, the inhibition of sucrose catabolism in sugarbeet and the inhibition of starch degradation in potato.

DESCRIPTION OF THE FIGURES

FIG. 1. Sprouting behaviour of patatin-TPS tubers with or without treatment with gibberellic acid (GA) after 14 days (FIG. 1A) and after 25 days (FIG. 1B).

DETAILED DESCRIPTION OF THE INVENTION

For definition purposes only the general term of a transformed plant is a plant totality or a plant grouping. This term is meant to cover a broad spectrum of plants and is not confined to one specific variety.

The invention is concerned with a method for the pre- and/or postharvest inhibition of remobilisation of storage compounds. The remobilisation of storage compounds is the process that plants undertake to utilise the compounds that have been stored, generally in specialised storage organs. A typical example of such a mobilisation is the process of sprouting from storage organs such as tubers, bulbs or seeds.

Specifically, provided are methods for the inhibition of sprouting, preferably in vegetatively propagated plants and methods to restore sprouting capabilities again in plants that have been inhibited. Sprouting in this sense is defined as the formation of shoots, runners, stolons or suckers, especially from storage tissue.

The basis of this invention is found in the fact that it has been surprisingly found that expression of TPS inhibits sprouting. TPS is an enzyme which is active in the trehalose synthesis pathway, which is not presently known to play a role in sprouting tissue. However, it has been recently found (WO 97/42326) that the enzymes TPS and TPP are able to change dramatically the carbohydrate metabolic and photosynthetic capacity of tissues in which they are expressed. It has furthermore been found that the effects of TPP and TPS are opposite, i.e. by simultaneous expression no major effects on the plant physiology and phenotype can be observed. In said application it has additionally been found that by expressing TPS in the tuber also the effects of the 'cold sweetening' process can be diminished, because the proportion of reducing sugars is decreased at harvesting and after storage. Thus, taking also into regard the present invention, expression of TPS may improve the storage of potatoes in two ways: for cold storage the effect of diminishing the cold sweetening process is important, while for storage under more moderate temperature the prevention of sprouting prevails.

Thus, TPS is capable to prevent remobilisation of storage compounds. This is also applicable in other crops, such as chicory, which is subject to degradation of the inulin into other carbohydrates. Expression of TPS in the storage organs of chicory prevents catabolic degradation of the inulin. Similarly, sucrose breakdown in sugarbeet can be prevented. Thus, expression of TPS in the taproots of sugarbeet prevents the loss of sucrose during storage of the sugarbeets.

Generally, the anti-sprouting effect is obtained by the expression of the TPS gene preferably in the tissues which are prone to sprouting, such as the potato tuber. For specific expression in the potato tuber the patatin promoter or any other tuber-specific promoter may be used to drive the expression of the TPS gene. We have, however, noted that it is most important that the promoter is active at the end of the filling phase of the tuber and during storage of the tuber. If the tuber-specific promoter is not very active anymore at that point, the inhibitory effects of the expression of TPS will wane off, and a delay in sprouting instead of a complete inhibition of sprouting will be the result.

The TPS gene is encoding a trehalose phosphate synthase. Several genes coding for this enzyme are known and can be found in all kind of organisms (WO 97/42326). In the experiments sustaining the invention the gene derived from *Escherichia coli* is used, but also other genes coding for TPS, e.g. derived from yeast or plants, are equally useful. In other embodiments of the invention compounds neutralizing the effect of TPS such as trehalose phosphate phosphatase (TPP) are used. Also the gene coding for TPP is derived from *E. coli*, but it can equally well be derived from other organisms such as yeast, plants or even humans (WO 97/42326). Not only the TPP is useful to restore the effects of TPS but any enzyme capable of degrading trehalose-6-phosphate can be used. A further example of such an enzyme is trehalose-6-phosphate hydrolase (TreC). A gene coding for this enzyme can be derived from *E. coli* (Rimmele, M., and Boos, W., Trehalose-6-phosphate hydrolase of *Escherichia coil*. J. Bacteriol. 176, 5654–5664, 1994).

In its simplest form the invention is directed to inhibit pre- and postharvest remobilisation of storage compounds in a transgenic plant by transforming a plant with a recombinant DNA cassette which comprises the gene coding for TPS and optionally a selectable marker gene. More specifically such a method prevents sprouting. Restoration of sprouting can be obtained by neutralizing the effect of TPS. This can be achieved in a number of ways. The following are given by example but methods to inhibit the effect of TPS are not limited to these examples.

A first system of restoration of sprouting is to introduce next to the TPS gene a gene coding for TPP, which is able to overcome the anti-sprouting effects caused by the TPS. To prevent the constitutive expression of TPP it is envisaged to bring expression of TPP under control of an inducible promoter. Inducible promoters include any promoter capable of increasing the amount of gene product produced by a given gene, in response to exposure to an inducer. In the absence of an inducer the DNA sequence will not be transcribed. Typically, the factor that binds specifically to an inducible promoter to activate transcription is present in an inactive form which is then directly or indirectly converted to the active form by the inducer. The inducer may be a chemical agent such as a protein, metabolite (sugar, alcohol, etc.), a growth regulator, herbicide, or a phenolic compound or a physiological stress imposed directly by heat, salt, wounding, toxic elements etc., or indirectly through the action of a pathogen or disease agent such as a virus. A plant cell containing an inducible promoter may be exposed to an inducer by externally applying the inducer to the cell such as by spraying, watering, heating, or similar methods. Inducible promoters are known to those familiar with the art and several exist that could conceivably be used to drive expression of the TPP gene. Inducible promoters suitable for use in accordance with the present invention include, but are not limited to, the heat shock promoter, the mammalian steroid receptor system and any chemically inducible promoter. Examples of inducible promoters include the inducible 70 kD heat shock promoter of *Drosophila melanogaster* (Freeling, M. et al., Ann. Rev. Genet. 19, 297–323) and the alcohol dehydrogenase promoter which is induced by ethanol (Nagao, R. T. et al., in: Miflin, B. J. (ed.) Oxford Surveys of Plant Molecular and Cell Biology, Vol. 3., pp. 384–438, Oxford Univ. Press, 1986). A promoter that is inducible by a simple chemical is particularly useful. Examples for the last category are the promoters described in WO 90/08826, WO 93/21334, WO 93/031294 and WO 96/37609.

Thus, the anti-sprouting effect can be restored by treatment with the inducer, and these restored sprouting lines can be used to propagate the seeding material, such as seed-potatoes. Without the presence of the inducer, sprouting of the offspring is still inhibited by the expression of TPS. This thus also functions as a way to produce germplasm protection.

A further method to restore the original sprouting phenotype again is to provide the plant with a recombinant DNA cassette which comprises next to the TPS gene an antisense TPS gene, said antisense gene being under control of an inducible promoter. As with the above-mentioned example on the induction of TPP also the antisense TPS is capable of negating the effect of the (sense) TPS expression because by annealing with the TPS mRNA it prevents successful translation of the TPS and thus inhibits the anti-sprouting effect.

A third system of restoration of the original sprouting phenotype is by introducing the DNA coding for a suppressor protein, said suppressor capable of suppressing the expression of TPS, while the expression of the suppressor is under control of an inducible promoter. Such a suppression can for instance be accomplished by use of the tet-repressor system, where a specific binding site, which can be recognized by the repressor, is introduced near the RNA-polymerase binding site of the gene which expression needs to be suppressed. If the tet-repressor is available then this repressor will bind to the specific sequence and thus, by steric hindrance, prevents the RNA-polymerase to initiate transcription. The gene coding for the tet-repressor can be adjacent the gene which expression should be controlled, but this is not necessary.

When the gene for the repressor is put under control of an inducible promoter the expression of the suppressor-molecule and thus the suppression of the TPS gene can be induced by applying an external inducer. Then, the TPS effect will not be established and normal sprouting will be the result.

A further system to restore the normal phenotype is to provide the gene coding for TPS or the expression cassette comprising said gene flanked by two site-specific recombination sites, which can be recognized by the corresponding recombinase.

A number of different site-specific recombinase systems can be utilized in accordance with the present invention, including but not limited to the Cre/lox system of bacteriophage P1, the FLP/FRT system of yeast, the Gin recombinase of phage Mu, the Pin recombinase of E. coli, and the R/RS system of the pSR1 plasmid. The two most used site-specific recombinase systems are the bacteriophage P1 cre/lox and the yeast FLP/FRT systems. In these systems a recombinase (Cre or FLP) interacts specifically with its respective site-specific recombination sequence (lox or FRT, respectively) to invert or excise the intervening sequences. The site-specific recombination sequence for each of those two systems is relatively short (34 bp for lox and 34–47 bp for FRT). Use of such a site-specific recombinase in plants is for instance described in U.S. Pat. No. 5,527,695. The DNA to be excised can be flanked by direct repeats of the site-specific recombination site, and subsequent introduction of the recombinase activity excises the DNA (and thus restores the original phenotype). The FLP/FRT recombinase system has been demonstrated to function efficiently in plant cells. Although the site-specific recombination sequences must be linked to the ends of the DNA sequence to be excised or inverted, the gene encoding the site-specific recombinase may be located elsewhere and thus can be separately introduced into the plant cells through standard transformation procedures, or through cross-pollination with a plant that already is capable of expressing the recombinase gene.

However, upon this last method of restoration the TPS gene is lost from the transgenic plants.

Other ways to remove the inhibitory effects of the expression of the TPS gene on the remobilisation of storage compounds are external treatments of the storage organs with compounds that are capable of neutralizing the effects of the expression of the TPS gene. Surprisingly, we have found that treatment with gibberellic acid (GA) was able to induce sprouting in potato tubers containing the TPS gene. This was accomplished by incubation of whole tubers or cut pieces in a solution of commercially available GA. It is, however, envisaged that the method of treatment can be varied and that for instance spraying of tubers with a GA solution would yield comparable results. Depending on the way of application the concentration of GA in the solution should be in the range of 0.1 to 10,000 ppm. It is further believed that the effect of GA is a neutralization of the effects of expression of the TPS gene. Therefor, it is envisaged that also in other examples of inhibition of remobilisation of storage compounds, treatment with GA will be able to restore the inhibitory effects of the expression of TPS.

Also surprisingly, we have found that wounding of potato tubers (through cutting off pieces containing at least one active meristem) alone was sufficient to induce sprouting of those pieces.

The recombinant DNA constructs of the present invention can be constructed using recombinant DNA technology known to those skilled in the art. The recombinant gene constructs can be inserted into vectors, which can be commercially available, specifically suited for transformation to plants and to express the gene product in the transformed cells. Transformed cells (those containing the recombinant DNA inserted into the host cell's DNA) are selected from untransformed cells through the use of a selectable marker included as part of the introduced recombinant DNA. Selectable markers include genes that provide antibiotic or herbicide resistance. Those cells containing the recombinant DNA are capable of surviving in the presence of antibiotic or herbicide concentrations that kill untransformed cells. Examples of selectable marker genes include the bar gene which provides resistance to the herbicide Basta, the nptII gene which confers kanamycin resistance, the hpt gene which confers hygromycin resistance and the cah gene which gives resistance to cyanamid. An entire plant can be generated from a single transformed plant cell through cell culturing techniques known to those skilled in the art.

With regard to the applicability of the invention in different plant species, it has to be mentioned that one particular embodiment of the invention is merely illustrated with transgenic potato plants as an example, the actual applicability being in fact not limited to this plant species. Any plant species can be provided with a recombinant DNA sequence according to the invention, but preferably plant species which are normally vegetatively propagated are especially useful.

Although some of the embodiments of the invention may not be practicable at present, e.g. because some plant species are as yet recalcitrant to genetic transformation, the practicing of the invention in such plant species is merely a matter of time and not a matter of principle, because the amenability to genetic transformation as such is of no relevance to the underlying embodiment of the invention.

Transformation of plant species is now routine for an impressive number of plant species, including both the Dicotyledoneae as well as the Monocotyledoneae. In principle any transformation method may be used to introduce recombinant DNA according to the invention into a suitable ancestor cell, as long as the cells are capable of being regenerated into whole plants. Methods may suitably be selected from the calcium/polyethylene glycol method for protoplasts (Krens, F. A. et al., 1982, Nature 296, 72–74; Negrutiu I. et al, June 1987, Plant Mol. Biol. 8, 363–373), electroporation of protoplasts (Shillito R. D. et al., 1985 Bio/Technol. 3, 1099–1102), microinjection into plant material (Crossway A. et al., 1986, Mol. Gen. Genet. 202, 179–185), (DNA or RNA-coated) particle bombardment of various plant material (Klein T. M. et al., 1987, Nature 327, 70), infection with (non-integrative) viruses and the like. A preferred method according to the invention comprises Agrobacterium-mediated DNA transfer. Especially preferred is the use of the so-called binary vector technology as disclosed in EP A 120 516 and U.S. Pat. No. 4,940,838). Tomato transformation can be preferably done essentially as described by Van Roekel et al. (Van Roekel, J. S. C., Damm, B., Melchers, L. S., Hoekema, A. (1993). Factors influencing transformation frequency of tomato (*Lycopersicon esculentum*). Plant Cell Reports, 12, 644–647). Potato transformation can be preferably done essentially as described by Hoekema et al. (Hoekema, A., Huisman, M. J., Molendijk, L., van den Elzen, P. J. M., and Cornelissen, B. J. C. (1989). The genetic engineering of two commercial potato cultivars for resistance to potato virus X. Bio/Technology 7, 273–278). Generally, after transformation plant cells or cell groupings are selected for the presence of one or more markers which are encoded by plant expressible genes co-transferred with the nucleic acid sequence encoding the protein according to the invention, whereafter the transformed material is regenerated into a whole plant.

Although considered somewhat more recalcitrant towards genetic transformation, monocotyledonous plants are amenable to transformation and fertile transgenic plants can be regenerated from transformed cells or embryos, or other plant material. Presently, preferred methods for transformation of monocots are microprojectile bombardment of embryos, explants or suspension cells, and direct DNA uptake or electroporation (Shimamoto, et al, 1989, Nature 338, 274–276). Transgenic maize plants have been obtained by introducing the Streptomyces hygroscopicus bar-gene, which encodes phosphinothricin acetyltransferase (an enzyme which inactivates the herbicide phosphinothricin), into embryogenic cells of a maize suspension culture by microprojectile bombardment (Gordon-Kamm, 1990, Plant Cell, 2, 603–618). The introduction of genetic material into aleurone protoplasts of other monocot crops such as wheat and barley has been reported (Lee, 1989, Plant Mol. Biol. 13, 21–30). Wheat plants have been regenerated from embryogenic suspension culture by selecting only the aged compact and nodular embryogenic callus tissues for the establishment of the embryogenic suspension cultures (Vasil, 1990 Bio/Technol. 8, 429–434). The combination with transformation systems for these crops enables the application of the present invention to monocots.

Monocotyledonous plants, including commercially important crops such as rice, banana and corn are also amenable to DNA transfer by Agrobacterium strains (vide WO 94/00977; EP 0 159 418 B1; Gould J, Michael D, Hasegawa O, Ulian E C, Peterson G, Smith R H, (1991) Plant. Physiol. 95, 426–434).

Following DNA transfer and regeneration, putatively transformed plants may be evaluated, for instance using Southern analysis, for the presence of the recombinant DNA according to the invention, copy number and/or genomic organization. In addition, or alternatively, expression levels of the newly introduced DNA may be undertaken, using Northern and/or Western analysis, techniques well known to persons having ordinary skill in the art. After the initial analysis, which is optional, transformed plants showing the desired copy number and expression level of the newly introduced recombinant DNA according to the invention may be tested for their male sterility or restoration to fertility. Alternatively, the selected plants may be subjected to another round of transformation, for instance to introduce further genes, such as the antisense TPS gene, the TPP gene or the suppressor gene.

To obtain transgenic plants capable of constitutively expressing more than one chimeric gene, a number of alternatives are available including the following:

A. The use of DNA, e.g a T-DNA on a binary plasmid, with a number of modified genes physically coupled to a selectable marker gene. The advantage of this method is that the chimeric genes are physically coupled and therefore migrate as a single Mendelian locus.
B. Cross-pollination of transgenic plants each already capable of expressing one or more chimeric genes, preferably coupled to a selectable marker gene, with pollen from a transgenic plant which contains one or more chimeric genes coupled to another selectable marker. Afterwards the seed, which is obtained by this crossing, maybe selected on the basis of the presence of the two selectable markers, or on the basis of the presence of the chimeric genes themselves. The plants obtained from the selected seeds can afterwards be used for further crossing. In principle the chimeric genes are not on a single locus and the genes may therefore segregate as independent loci.
C. The use of a number of a plurality chimeric DNA molecules, e.g. plasmids, each having one or more chimeric genes and a selectable marker. If the frequency of co-transformation is high, then selection on the basis of only one marker is sufficient. In other cases, the selection on the basis of more than one marker is preferred.
D. Consecutive transformation of transgenic plants already containing a first, second, (etc.), chimeric gene with new chimeric DNA, optionally comprising a selectable marker gene. As in method B, the chimeric genes are in principle not on a single locus and the chimeric genes may therefore segregate as independent loci.
E. Combinations of the above mentioned strategies.

Plants, in which this invention is particularly useful, are plants which are able to propagate vegetatively and in which sprouting at a certain moment is an undesired property. The most outstanding examples are potato and onion, but the invention can also be used in flower bulbs, strawberries and banana. Next to the complete inhibition of sprouting and an inducible restoration mechanism, it is also envisaged that the inhibition can be made inducible. This, for instance, would be useful in strawberry and banana, where sprouting is a desired property for the multiplication of plants, but where sprouting can be competitive with regard to other processes such as fruit ripening. If the TPS gene is placed under control of an inducible promoter it is possible to inhibit sprouting at any time during the growing of the crops, for instance during the period of seed setting or fruit ripening. Preferably such an induction of expression of the TPS gene is performed by a chemical inducible promoter which reacts on the (external) application of a chemical substance. Furthermore, in this embodiment of the invention it would be preferable also to make the expression of TPS tissue specific for meristematic tissue. Promoters, which are specific for meristematic tissue are readily available in the art (for instance the HMG2 promoter from Enjuto et al., Plant Cell 7, 517, 1995 and the rice PCNA promoter from Kosugi et al., Plant J. 7, 877, 1995).

Next to the sprouting the mechanism of inhibition of pre- and postharvest remobilisation of storage compounds is also of use in chicory to prevent degradation of inulin and in sugarbeet to prevent degradation of sucrose.

The following examples are further provided for illustrative purposes only and are in no way intended to limit the scope of the present invention.

Standard methods for the isolation, manipulation and amplification of DNA, as well as suitable vectors for replication of recombinant DNA, suitable bacterium strains, selection markers, media and the like are described for instance in Sambrook, J., Fritsch, E. F., and Maniatis, T. (1989) Molecular cloning; a laboratory manual. Cold Spring Harbor Laboratory Press, Cold Spring Harbor, N.Y.; DNA Cloning: Volumes I and II (D. N. Glover ed. 1985); and in: From Genes To Clones (E.-L. Winnacker ed. 1987).

DNA Manipulations

All DNA procedures (DNA isolation from E.coli, restriction, ligation, transformation, etc.) are performed according to standard protocols (Sambrook et al. (1989) Molecular Cloning: a laboratory manual, 2nd ed. Cold Spring Harbor Laboratory Press, CSH, New York).

Strains

In all examples E.coli K-12 strain DH5α is used for cloning. The Agrobacterium tumefaciens strains used for plant transformation experiments are EHA 105 and MOG 101 (Hood et al., Trans. Research 2, 208–218, 1993) Generation of Potato Plants Transgenic for pat-TPS Construction of pMOG845 harboring the *E. coli* tps gene under control of the tuber-specific patatin promoter, triparental mating to Agrobacterium and the generation of transgenic potato plants, *Solanum tuberosum* cv. kardal, are described in WO 97/42326.

EXAMPLE 1

In one part of the experiment, tuber material was produced from in vitro potato plants transgenic for pMOG845 (patatin-tps). A field trial experiment was set-up using tubers of 9 independent transgenic lines, 3 plots per line, 5 tubers per plot. Tubers were transferred to the field at the beginning of May and the sprouting process was monitored on a regular basis. Results are depicted in table 1. In the second part of the experiment pat-TPS plants (var. Kardal) derived from tissue culture plants were grown in the phytochamber under 500 µmol quanta $m^{-2} s^{-1}$ (16 h light, 20° C.; 8 h dark (15° C.)). Tubers were harvested after three months and stored in the cold (4° C.) for 2 months. Then they were transferred to room temperature (RT) and sprouting was assessed during a period of four weeks.

TABLE 1

| Plant-line | Sprouting Field | Phytochamber |
| --- | --- | --- |
| Kardal | all tubers | all tubers |
| 845-17 | all tubers* | delayed |
| 845-13 | all tubers | all tubers |
| 845-28 | none | none |
| 845-4 | all tubers | all tubers |
| 845-11 | none | none |
| 845-22 | 2/15 tubers | none |
| 845-2 | all tubers* | delayed |
| 845-1 | all tubers* | delayed |
| 845-25 | all tubers | all tubers |

*means that the plants in that plot were significantly smaller compared to wild-type indicating a delay in sprouting.
Delayed means that no sprouts were visible after 2 week transfer to RT after a 2 month cold period. None means sprouting does not occur within 4 weeks.

Tubers revealing the complete absence of sprouting have been shown to have a high expression level of the transgene. A reduction of cold-sweetening as described in WO 97/42326 is observed in the non-sprouting sprouting lines and to a lesser extent in the tubers delayed in sprouting or normal sprouting tubers.

EXAMPLE 2

Gibberellic Acid Reverts Anti-sprouting Phenotype

Whole tubers obtained from the plants of Example 1 grown under phytochamber conditions were taken. Approximately 1 week after transfer to RT they were incubated for 24 h in a solution containing 0.17% (w/v) gibberellic acid (GA 4 and GA 7; formulation commercially available as Berelex®, Zeneca, Ridderkerk, Netherlands). Control tubers were not incubated. Further storage was done at RT. The induction of sprouting occurred in GA-treated and non-treated wildtype tubers after 8 days. After 14 days, 95% of the 14 non-treated wildtype tubers sprouted, while none of the transgenic lines did (FIG. 1A). In contrast, all tubers (5) from GA-treated wildtype tubers and 80%, 50%, 100% and 17% of the GA-treated transgenic tubers from lines 845-1, -17, -22, -28 form sprouts, respectively. All non-treated transgenic tubers did not sprout. After 25 days it can be seen that lines 845-1 and 845-17 show delayed sprouting in the non-treated tubers (FIG. 1B).

EXAMPLE 3

Wounding Reverts Anti-sprouting Phenotype

Pat-TPS plants (Var. Kardal) derived from tissue culture plants were grown in the phytochamber under 500 µmol quanta $m^{-2} s^{-1}$ (16 h light, 20° C.; 8 h dark (15° C.)). Tubers were harvested after three months and stored in the cold (4° C.) for 2 months.

Three days after transfer to room temperature (RT), tuber pieces were cut with a knife containing at least one active meristem (eye). Cut pieces originating from 3–10 tubers per line were washed for 15 min in tap water. Approximately 6–10 pieces were subsequently incubated for 10 min on either water or on a 1, 10 or 1000 ppm solution of gibberellic acid (GA3, SIGMA, Zwijndrecht, Netherlands). All pieces from one treatment were transferred to containers onto wet paper tissue and covered with a plastic top to prevent drying out. Sprouting of wild-type and tps tuber pieces occurred within 4 days incubated either on water or on the different gibberellic acid solutions, indicating that wounding per se is sufficient to restore sprouting.

What is claimed is:

1. A method of inhibiting post-harvest sprouting of a potato tuber, said method comprising transforming a potato plant with a recombinant DNA encoding a bacterial trehalose phosphate synthase (TPS), growing said potato plant harvesting said tuber, and storing said tuber for a time sufficient to exhibit inhibited post-harvest sprouting in comparison to a tuber from a potato plant not comprising said recombinant DNA.

2. The method according to claim 1, wherein said recombinant DNA is under the transcriptional control of a tuber-specific promoter.

3. The method according to claim 2, wherein said promoter is the patatin promoter.

4. The method according to claim 1, wherein said recombinant DNA is from *Escherichia coli*.

5. The method according to claim 1, wherein said recombinant DNA comprises a region encoding a selectable marker gene.

6. The method according to claim 5, wherein said selectable marker gene provides for resistance to a herbicide.

7. The method according to claim 1, wherein said potato plant is transformed by Agrobacterium-mediated transformation.

* * * * *